US00PP31900P2

(12) United States Plant Patent
Knosher

(10) Patent No.: US PP31,900 P2
(45) Date of Patent: Jun. 23, 2020

(54) ***DIGITALIS* PLANT NAMED 'BALROXOSE'**

(50) Latin Name: ***Digitalis* hybrid**
Varietal Denomination: Balroxose

(71) Applicant: Ball Horticultural Company, West Chicago, IL (US)

(72) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/602,335

(22) Filed: Sep. 16, 2019

(51) Int. Cl.
*A01H 5/02* (2018.01)
*A01H 6/68* (2018.01)

(52) U.S. Cl.
USPC ..... Plt./263.1

(58) Field of Classification Search
USPC ..... Plt./263.1
CPC ..... A01H 5/02; A01H 6/68
See application file for complete search history.

(56) References Cited

PUBLICATIONS

Meet Me There Farwest Portland 2019 New Varieties Showcase Aug. 21-23, 2019.*

* cited by examiner

*Primary Examiner* — Annette H Para
(74) *Attorney, Agent, or Firm* — Audrey Charles

(57) ABSTRACT

A new and distinct cultivar of *Digitalis* plant named 'Balroxose', characterized by its medium purplish-red colored flowers, dark green-colored foliage, and moderately vigorous, columnar-upright growth habit, is disclosed.

1 Drawing Sheet

Latin name of genus and species of plant claimed: *Digitalis* hybrid.

Variety denomination: 'Balroxose'.

BACKGROUND OF THE INVENTION

The present invention relates to a new and distinct cultivar of *Digitalis* plant botanically known as *Digitalis* hybrid and hereinafter referred to by the cultivar name 'Balroxose'.

The new cultivar originated in a controlled breeding program in Elburn, Ill. during September 2008. The objective of the breeding program was the development of perennial *Digitalis* cultivars having unique flower coloration.

The new *Digitalis* cultivar is the result of cross-pollination. The female (seed) parent of the new cultivar is the proprietary *Digitalis purpurea* breeding selection coded 948-5, not patented, characterized by its dark pink-colored flowers, medium green-colored foliage, and moderately vigorous, columnar-upright growth habit. The male (pollen) parent of the new cultivar is the proprietary *Digitalis floribunda* breeding selection coded 938-1, not patented, characterized by its light yellow-colored flowers, medium green-colored foliage, and moderately vigorous, columnar-upright growth habit. The new cultivar was discovered and selected as a single flowering plant within the progeny of the above stated cross-pollination during September 2010 in a controlled environment in Elburn, Ill.

Asexual reproduction of the new cultivar by terminal stem cuttings since September 2010 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balroxose' as a new and distinct cultivar of *Digitalis* plant:

1. Medium purplish-red colored flowers;
2. Dark green-colored foliage; and
3. Moderately vigorous, columnar-upright growth habit.

Plants of the new cultivar differ from plants of the female parent primarily in having purplish-red colored flowers, and more branches per plant. Plants of the new cultivar differ from plants of the male parent primarily in having purplish-red colored flowers, larger sized leaves and slightly increased growth vigor.

Of the many commercially available *Digitalis* cultivars, the most similar in comparison to the new cultivar is 'Takforoiv', U.S. Plant Pat. No. 26,554. However, in side-by-side comparison, plants of the new cultivar differ from plants of 'Takforoiv' in at least the following characteristics:

1. Plants of the new cultivar has a more greyed purplish red flower color than plants of 'Takforoiv';
2. Plants of the new cultivar have smaller flowers than plants of 'Takforoiv'; and
3. Plants of the new cultivar are hardier than plants of 'Takforoiv'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balroxose'. The plants were approximately 4.5 months old and grown in 2-gallon containers for approximately 12 weeks in an outdoor nursery environment in West Chicago, Ill.

DETAILED BOTANICAL DESCRIPTION

Figure 1:
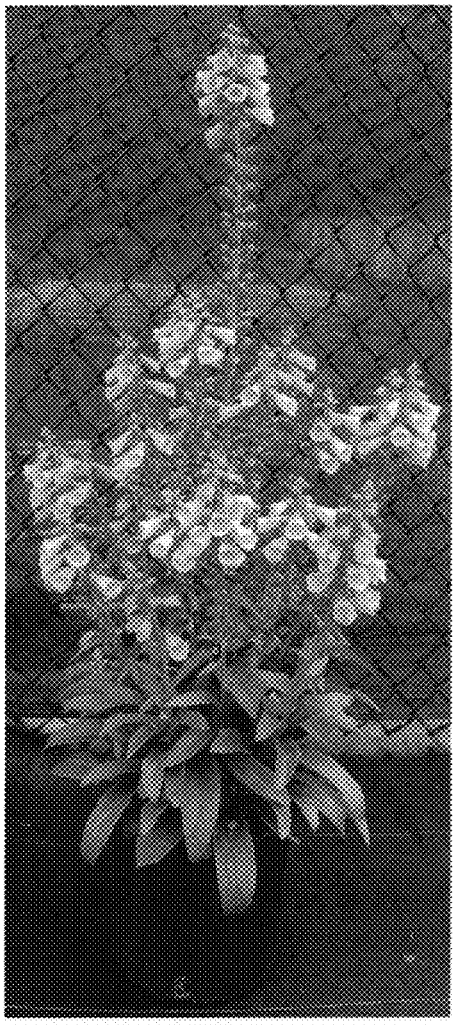
FIG. 1 illustrates a side view of the overall growth and flowering habit of 'Balroxose'.
Figure 2:
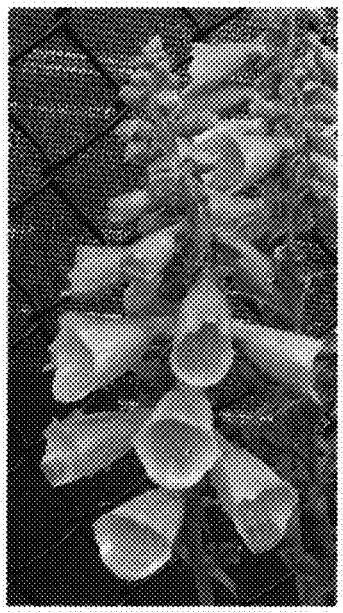
FIG. 2 illustrates a close-up view of an individual inflorescence of 'Balroxose'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2019 under natural light conditions in West Chicago, Ill.

The following descriptions and measurements describe approximately 4.5-month old plants produced from cuttings from stock plants and grown in a glass-covered greenhouse under conditions comparable to those used in commercial practice. After approximately 10 weeks rooted plants were transplanted into 2-gallon containers utilizing a soilless growth medium. Plants were then transferred to an outdoor nursery environment in West Chicago, Ill. and grown for approximately 12 weeks. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Digitalis* hybrid 'Balroxose'.

Parentage:

*Female parent*.—Proprietary *Digitalis purpurea* breeding selection coded 948-5, not patented.

*Male parent*.—Proprietary *Digitalis floribunda* breeding selection coded 938-1, not patented.

Propagation:

*Type cutting*.—Terminal stem.

*Time to initiate roots*.—Approximately 15 to 20 days.

*Time to produce a rooted cutting*.—Approximately 42 to 49 days.

*Root description*.—Fine, fibrous.

*Rooting habit*.—Freely branching.

Plant description:

*Commercial crop time*.—Approximately 12 to 14 weeks from a rooted cutting to finish in a 15 cm pot, vernalization not required.

*Growth habit and general appearance*.—Herbaceous perennial, moderately vigorous, columnar-upright.

*Hardiness*.—Hardiness. — USDA Zone 5a (−20° F. to −15° F./−28.9 ° C. to −26° C.).

*Size*.—Height from soil level to top of plant plane: Approximately 90.0 cm. Width: Approximately 42.0 cm.

*Branching habit*.—Freely branching. Quantity of branches per plant: Approximately 1 main branch, with approximately 4 basal clumps.

*Main branch*.—Strength: Strong. Aspect: Erect. Length to base of inflorescence: Approximately 22.0 cm. Diameter: Approximately 1.0 cm. Length of central internode: Approximately 5.0 cm. Texture: Densely glandular pubescent. Gland color: Colorless, transparent. Color of young stem: 144A. Color of mature stem: 144B to 144A.

Foliage description:

*General description*.—Quantity of leaves per main branch: Approximately 11. Fragrance: None. Form: Simple. Arrangement: Rosette at plant base and dextrorse on flowering stems.

*Leaves*.—Aspect: Perpendicular or obtuse angle to stem. Shape: Elliptic to narrow elliptic. Margin: Senate. Apex: Acute. Base: Attenuate, cauline leaves sessile. Venation pattern: Pinnate. Length of mature leaf: Approximately 13.0 cm. Width of mature leaf: Approximately 6.0 cm. Texture of upper surface: Rugous, densely pubescent. Texture of lower surface: Densely pubescent on venation. Color of upper surface of young foliage: 137A with venation of 146C. Color of lower surface of young and mature foliage: Closest to 138B with venation of 146D and midvein of closest to 145D. Color of upper surface of mature foliage: NN137A with venation of 146C.

*Petiole*.—Length: Approximately 6.0 cm. Diameter: Approximately 9.0 mm. Texture: Densely pubescent. Color: Closest to 146D.

Flowering description:

*Flowering habit*.—'Balroxose' is a long-day facultative, freely flowering under outdoor growing conditions, blooming from April through September.

*Lastingness of individual flower on the plant*.—Approximately 10 days.

Inflorescence description:

*General description*.—Type: Terminal raceme. Aspect: Primarily erect. Quantity per plant: Approximately 12. Fragrance: None. Length or height: Approximately 28.0 cm. Width: Approximately 8.0 cm. Quantity of fully open flowers per inflorescence: Approximately 12.

*Peduncle*.—Strength: Strong. Aspect: Erect. Length: Approximately 19.0 cm. Diameter: Approximately 4.0 mm to 8.0 mm. Texture: Densely glandular pubescent. Gland color: Colorless, transparent. Color: 144B to 144A.

Flower description:

*Type*.—Single, campanulate, not persistent.

*Bud just before opening*.—Shape: Ovoid. Length: Approximately 1.6 cm. Diameter: Approximately 8.0 mm. Color: Calyx of 146B, petal portion 144D tinted with 186A at apex.

*Corolla*.—Shape: Bilabiate. Aspect: Facing outward and downward. Length: Approximately 2.1 cm. Width: Approximately 2.4 cm. Depth: Approximately 3.8 cm.

*Petals*.—Quantity: 5 petals fused at base forming a throat and consisting of an upper lip with three lobes and a single-lobed projecting lower lip. Shape: Obovate. Margin: Entire, ciliate. Apex: Obtuse, with lateral lobes notched and lower lobe slightly rolled under.

*Upper lip*.—Length of upper lobe from throat: Approximately 3.0 mm. Width of upper lobe: Approximately 1.6 cm. Length of lateral lobes from throat: Approximately 4.0 mm. Width of lateral lobes: Approximately 1.1 cm. Texture of upper (inner) surface: Glabrous. Texture of lower (outer)

surface: Sparsely glandular pubescent. Gland color: Colorless, transparent. Color of upper (inner) surface when fully open: 158C with a faint and patchy overlay of 186C. Color of lower (outer) surface when fully open: 186B to 186C.

*Lower lip*.—Length of lobe from throat: Approximately 8.0 mm. Width: Approximately 1.8 cm. Texture of upper (inner) surface: Sparsely pubescent. Texture of lower (outer) surface: Moderately glandular pubescent. Gland color: Colorless, transparent. Color of upper (inner) surface when fully open: 158C with an overlay of 186B. Color of lower (outer) surface when fully open: 158C with an overlay of 186C.

*Corolla tube*.—Length: Approximately 3.5 cm. Width: Approximately 1.9 cm. Texture of inner surface: Sparsely pubescent on lower portion (nectar glide). Texture of outer surface: Glabrous. Color of inner surface: 158C with a faint and patchy overlay of 186C, spots of 79A forming nectar glide beginning at lower lip. Color of outer surface: 186A and lower portion of 186B to 186C with irregular spots of 158C.

*Calyx*.—Shape: Cupped, tips flare out with age. Diameter: Approximately 1.7 cm.

*Sepals*.—Quantity per flower: 5, imbricate. Shape: Lanceolate. Apex: Acute. Base: Truncate. Length: Approximately 1.1 cm. Width: Approximately 6.0 mm. Texture of upper and lower surfaces: Densely pubescent. Color of upper (inner) and lower (outer) surfaces: 137A.

*Pedicel*.—Strength: Strong. Aspect: Acute angle to stem. Length: Approximately 5.0 mm. Diameter: Approximately 1.0 mm. Texture: Densely glandular pubescent. Gland color: Colorless, transparent. Color: 144A.

*Reproductive organs*.—Androecium: Stamen quantity: 4, basifixed. Stamen length: Longer pair at approximately 2.6 cm and shorter pair at 1.9 cm. Filament length of fixed portion: Approximately 1.1 cm. Filament color: 155D. Anther shape: Reniform. Anther length: Approximately 3.0 mm. Anther color: 154C. Pollen amount: Sparce. Pollen color: 155D. Gynoecium: Pistil quantity: 1 per flower. Pistil length: Approximately 2.3 cm. Stigma shape: Bifid. Stigma length: Approximately 1.0 mm. Stigma color: 155D. Style length: Approximately 1.4 cm. Style color: NN155A with a faint overlay of 145D, near stigma. Ovary length: Approximately 8.0 mm. Ovary texture: Densely pubescent. Ovary color: 144C.

Seed and fruit production: Neither seed nor fruit production has been observed.

Disease and pest resistance: Resistance to pathogens and pests common to *Digitalis* has not been observed.

What is claimed is:

1. A new and distinct cultivar of *Digitalis* plant named 'Balroxose', substantially as herein illustrated and described.

* * * * *